(12) United States Patent
Kaiami et al.

(10) Patent No.: US 9,149,201 B2
(45) Date of Patent: Oct. 6, 2015

(54) TWA MEASURING APPARATUS AND TWA MEASURING METHOD

(71) Applicant: NIHON KOHDEN CORPORATION, Tokyo (JP)

(72) Inventors: Takashi Kaiami, Tokyo (JP); Tsuneo Takayanagi, Tokyo (JP); Masato Tanaka, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 0 days.

(21) Appl. No.: 13/848,787

(22) Filed: Mar. 22, 2013

(65) Prior Publication Data
US 2013/0261480 A1 Oct. 3, 2013

(30) Foreign Application Priority Data

Mar. 30, 2012 (JP) ................................ 2012-081478

(51) Int. Cl.
*A61B 5/0472* (2006.01)
*A61B 5/00* (2006.01)
*A61B 5/0452* (2006.01)

(52) U.S. Cl.
CPC .............. *A61B 5/0472* (2013.01); *A61B 5/0452* (2013.01); *A61B 5/7246* (2013.01)

(58) Field of Classification Search
CPC ............. A61B 5/0464; A61B 5/04525; A61B 5/0472; A61B 5/0452; A61B 5/7246
USPC ......................................................... 600/509
See application file for complete search history.

(56) References Cited

U.S. PATENT DOCUMENTS

| 5,713,367 | A | * | 2/1998 | Arnold et al. | ................. | 600/517 |
| 5,935,082 | A | * | 8/1999 | Albrecht et al. | .............. | 600/515 |
| 6,169,919 | B1 | * | 1/2001 | Nearing et al. | ................ | 600/518 |

(Continued)

FOREIGN PATENT DOCUMENTS

| CN | 1387823 A | 1/2003 |
| CN | 1520777 A | 8/2004 |

(Continued)

OTHER PUBLICATIONS

Extended European Search Report, dated Aug. 1, 2013, issued by the European Patent Office in counterpart European Application No. 13160695.6.
Nemati, S et al "A Nonparametric Surrogate-Based Test of Significance for T-Wave Alternans Detection," IEEE Transactions on Biomedical Engineering, vol. 58, No. 5, May 1, 2011, pp. 1356-1364.

(Continued)

*Primary Examiner* — Carl H Layno
*Assistant Examiner* — Erin Piateski
(74) *Attorney, Agent, or Firm* — Sughrue Mion, PLLC

(57) ABSTRACT

A TWA measuring apparatus includes: a grouping section which is configured to group electrocardiogram waveforms of a subject in increments of a first beat number, to generate a plurality of first groups; a storage section which is configured to store the electrocardiogram waveforms; a testing section which is configured to test a statistical intergroup difference of measurement values of the electrocardiogram waveforms of the first groups; a heartbeat condition determining section which is configured to determine that a heartbeat condition is unstable, when a significant statistical difference exists between the first groups; and a TWA measuring section which is configured to measure variation in heartbeat by using the stored electrocardiogram waveforms, when it is determined that the heartbeat condition is unstable.

18 Claims, 12 Drawing Sheets

(56) References Cited

U.S. PATENT DOCUMENTS

| | | |
|---|---|---|
| 6,668,189 B2 | 12/2003 | Kaiser et al. |
| 7,142,907 B2 | 11/2006 | Xue et al. |
| 7,174,204 B2 | 2/2007 | Hadley et al. |
| 2003/0060724 A1* | 3/2003 | Thiagarajan et al. ......... 600/515 |
| 2004/0162498 A1 | 8/2004 | Kaiser et al. |
| 2005/0234363 A1 | 10/2005 | Xue |
| 2006/0173371 A1 | 8/2006 | Xue |
| 2006/0173372 A1 | 8/2006 | Xue |
| 2010/0036271 A1* | 2/2010 | Wirasinghe et al. .......... 600/510 |
| 2011/0245700 A1 | 10/2011 | Ghanem et al. |
| 2011/0270105 A1* | 11/2011 | Wirasinghe et al. .......... 600/515 |

FOREIGN PATENT DOCUMENTS

| | | |
|---|---|---|
| CN | 1682654 A | 10/2005 |
| WO | 03005879 A2 | 1/2003 |

OTHER PUBLICATIONS

Bloomfield, Daniel M et al: "Interpretation and Classification of Microvolt T Wave Alternans Tests", Journal of Cardiovascular Electrophysiology, vol. 13, No. 5, May 1, 2002, pp. 502-512.

Myles, Rachel C., et al., "Is Microvolt T-Wave Alternans the Answer to Risk Stratification in Heart Failure?," Circulation, Journal of the American Heart Association, Dec. 18/25, 2007, 116, doi: 10.1161/CIRCULATIONAHA.107.699918, pp. 2984-2991.

Salerno-Uriarte, et al., "Prognostic Value of T-Wave Alternans in Patients With Heart Failure Due to Nonischemic Cardiomyopathy: Results of the ALPHA Study," Journal of the American College of Cardiology, vol. 50, No. 19, Nov. 6, 2007, pp. 1896-1904.

Office Action dated May 28, 2014 issued by the European Patent Office in corresponding European Application No. 13 160 695.6.

Office Action dated Mar. 19, 2015 issued by the State Intellectual Property of the People's Republic of China in counterpart Chinese Patent Application No. 201310095104.0.

* cited by examiner

TWA MEASURING APPARATUS AND TWA MEASURING METHOD

CROSS-REFERENCE TO RELATED APPLICATION(S)

This application is based upon and claims the benefit of priority from prior Japanese patent application No. 2012-081478, filed on Mar. 30, 2012, the entire contents of which are incorporated herein by reference.

BACKGROUND

The presently disclosed subject matter relates to a TWA measuring apparatus and TWA measuring method which can accurately measure the presence of TWA (T-wave alternans).

TWA appears at onset of illness such as QT prolongation syndrome, variant angina, acute myocardial ischemia, electrolyte abnormality, paroxysmal tachycardia, bradycardia, or pericardial fluid accumulation. TWA is a phenomenon in which the amplitude and polarity of the T wave appearing in an electrocardiogram are alternately changed, and an index effective to predict sudden cardiac death. TWA is not a phenomenon which can be always observed with the naked eye, and therefore its application in clinics is limited.

From the 1980s, consequently, techniques for enabling minute TWA (Microvolt TWA: MTWA) to be measured by a computer have been developed.

Examples of currently proposed techniques for measuring TWA are a measurement technique based on the MMA (Modified Moving Average) method of General Electric (GE) Company, and that based on the periodogram of Cambridge Heart (CH), Inc. which are disclosed in U.S. Pat. No. 6,668,189 and U.S. Pat. No. 5,935,082, respectively.

The measurement technique of GE Company is directed to a method of analyzing a time waveform in a time region, and is said to have resistance to noises. However, the technique does not have a long history as a measurement technique, and it is required to watch its clinical effect.

By contrast, the measurement technique of CH Inc. which is a technique in a frequency region has been used from the 1980s, and hence its effectiveness in clinics has been proved. Today, therefore, it is considered that the measurement technique based on the periodogram of CH Inc. is clinically more useful than that based on the MMA method of GE Company.

With respect to the measurement technique based on the periodogram of CH Inc., after its announcement, various techniques for performing new processes, such as a technique of measurement electrodes are added, and still now the added latest techniques have been used.

In the technique of measuring TWA, a value (alternans voltage) indicative of the magnitude of TWA, and a value (alternans rate) indicative of the reliability of the measurement of TWA are calculated, and, when the magnitude of the value indicative of the reliability of the measurement of TWA is equal to or larger than 3.0, it is determined that TWA exists.

The index in which the magnitude of the value indicative of the reliability of the measurement of TWA is equal to or larger than 3.0 was derived based on experimental results. In the case where noises are mixed in measured electrocardiogram waveforms, even when TWA exists, therefore, it is often that the magnitude of the value indicative of the reliability of the measurement of TWA is not equal to or larger than 3.0, and the determination is determined to be impossible.

As a result of a test for evaluating the existing technique of measuring TWA, it has been known that the rate of the determination which is determined to be impossible is from 10% to 40% (see is Microvolt T-wave Alternans the Answer to Risk Stratification in Heart Failure?: Circulation: 2007: 116: 2984-2991). With respect to a positive herd in which a group that is determined to be indeterminable is added to a group that is determined that TWA exists, and a negative herd configured by only a group that is determined that TWA does not exist, their prognoses (medical expectations for the disease process) were observed, and it has been found that the prognosis of the positive herd is worse than that of the negative herd (see Prognostic Value of T-wave Alternans in Patients With Heart Failure Due to Nonischemic Cardiomyopathy: J. Am. Coll. Cardiol: 2007: 50: 1896-1904).

Therefore, it is anticipated that a patient having a poor prognosis exists among patients who are determined to be indeterminable, and confusions occur in the interpretation of a determination result of indetermination.

SUMMARY

The presently disclosed subject matter may provide a TWA measuring apparatus and TWA measuring method which can accurately measure TWA.

The TWA measuring apparatus may comprise: a grouping section which is configured to group electrocardiogram waveforms of a subject in increments of a first beat number, to generate a plurality of first groups; a storage section which is configured to store the electrocardiogram waveforms; a testing section which is configured to test a statistical intergroup difference of measurement values of the electrocardiogram waveforms of the first groups; a heartbeat condition determining section which is configured to determine that a heartbeat condition is unstable, when a significant statistical difference exists between the first groups; and a TWA measuring section which is configured to measure variation in heartbeat by using the stored electrocardiogram waveforms, when it is determined that the heartbeat condition is unstable.

The electrocardiogram waveforms may be acquired from the patient, and the first beat number may be a constant beat number.

The electrocardiogram waveforms may be acquired from the patient, the grouping section may group the electrocardiogram waveforms in increments of a second beat number, which is different from the first beat number, to generate a plurality of second groups, the testing section may test a statistical intergroup difference of measurement values of the electrocardiogram waveforms of the second groups, and the heartbeat condition determining section may determine that the heartbeat condition is unstable, when a significant statistical difference exists between the first groups and a significant statistical difference does not exist between the second groups.

The TWA measuring apparatus may further comprise: an electrocardiogram data inputting section which is configured to input electrocardiogram data including the electrocardiogram waveforms of the subject, and the first beat number may be a constant beat number.

The TWA measuring apparatus may further comprise: an electrocardiogram data inputting section which is configured to input electrocardiogram data including the electrocardiogram waveforms of the subject, and the grouping section may group the electrocardiogram waveforms in increments of a second beat number, which is different from the first beat number, to generate a plurality of second groups, the testing section may test a statistical intergroup difference of measurement values of the electrocardiogram waveforms of the second groups, and the heartbeat condition determining section may determine that the heartbeat condition is unstable, when a significant statistical difference exists between the first groups and a significant statistical difference does not exist between the second groups.

The electrocardiogram waveforms grouped by the grouping section may be electrocardiogram waveforms of a constant beat number.

The first beat number may be a prime beat number.

Each of the first bean number and the second beat number may be a prime beat number.

The TWA measuring section may perform FFT processing on a constant number of electrocardiogram waveforms in the electrocardiogram waveforms stored in the storage section to calculate a periodogram, calculate an alternans value by using the calculated periodogram, and determine presence of TWA by using the alternans value.

The TWA measuring section may extract a constant number of electrocardiogram waveforms in the electrocardiogram waveforms stored in the storage section, produce typical waveforms of odd and even beats of the extracted electrocardiogram waveforms, and compare the typical waveforms of odd and even beats with each other, thereby determining presence of TWA.

The TWA measuring method may comprise: grouping electrocardiogram waveforms of a subject in increments of a first beat number, to generate a plurality of first groups; testing a statistical intergroup difference of measurement values of the electrocardiogram waveforms of the first groups; determining that a heartbeat condition is unstable, when a significant statistical difference exists between the first groups; and measuring variation in heartbeat by using the electrocardiogram waveforms, when it is determined that the heartbeat condition is unstable.

The TWA measuring method may further comprise: attaching measurement electrodes to acquire the electrocardiogram waveforms from the subject, and the first beat number may be a constant beat number.

The TWA measuring method may further comprise: attaching measurement electrodes to acquire the electrocardiogram waveforms from the subject; grouping the electrocardiogram waveforms in increments of a second beat number, which is different from the first beat number, to generate a plurality of second groups; and testing a statistical intergroup difference of measurement values of the electrocardiogram waveforms of the second groups, and it may be determined that the heartbeat condition is unstable, when a significant statistical difference exists between the first groups and a significant statistical difference does not exist between the second groups.

The TWA measuring method may further comprise: inputting electrocardiogram data including the electrocardiogram waveforms of the subject, and the first beat number may be a constant beat number.

The TWA measuring method may further comprise: inputting electrocardiogram data including the electrocardiogram waveforms of the subject; grouping the electrocardiogram waveforms in increments of a second beat number, which is different from the first beat number, to generate a plurality of second groups; and testing a statistical intergroup difference of measurement values of the electrocardiogram waveforms of the second groups, and it may be determined that the heartbeat condition is unstable, when a significant statistical difference exists between the first groups and a significant statistical difference does not exist between the second groups.

A process of measuring the variation in heartbeat may include: performing FFT processing on a constant number of electrocardiogram waveforms in the electrocardiogram waveforms to calculate a periodogram; calculating an alternans value by using the calculated periodogram; and determining presence of TWA by using the alternans value.

A process of measuring the variation in heartbeat may include: producing typical waveforms of odd and even beats by using a constant number of electrocardiogram waveforms in the electrocardiogram waveforms; and comparing the typical waveforms of odd and even beats with each other, thereby determining presence of TWA.

DETAILED DESCRIPTION OF EXEMPLARY EMBODIMENTS

The TWA measuring apparatus and TWA measuring method of the presently disclosed subject matter will be described in detail with respect to Embodiment 1 to Embodiment 4 with reference to the drawings.

When the TWA measuring apparatus and TWA measuring method of the presently disclosed subject matter are used, the presence of TWA can be accurately measured from an electrocardiographic signal which is obtained by various measuring methods.

Specifically, the presence of TWA can be measured from an electrocardiographic signal acquired by a measuring method such as a Frank's vector electrocardiogram, and a usual scalar electrocardiogram, i.e., a standard 12-lead electrocardiogram, a derived lead electrocardiogram, a Holter electrocardiogram, an event electrocardiogram, an exercise electrocardiogram, and a monitoring electrocardiogram.

In the specification, the term "patient" is used as a specific example of the subject. However, the patient means not only a patient who is examined in a hospital, but also a user of a facility other than a hospital, such as a detection center or clinic in which a physical examination is performed, or an ordinary house.

Embodiment 1

Hereinafter, a TWA measuring apparatus and TWA measuring method of Embodiment 1 will be described. In the embodiment, electrocardiogram waveforms acquired by measurement electrodes of an electrocardiogram are divided into two groups in increments of two beats, and a statistical difference of measurement values between the two groups are tested, thereby enabling TWA to be accurately measured.

(Configuration of TWA Measuring Apparatus)

Figure 1:
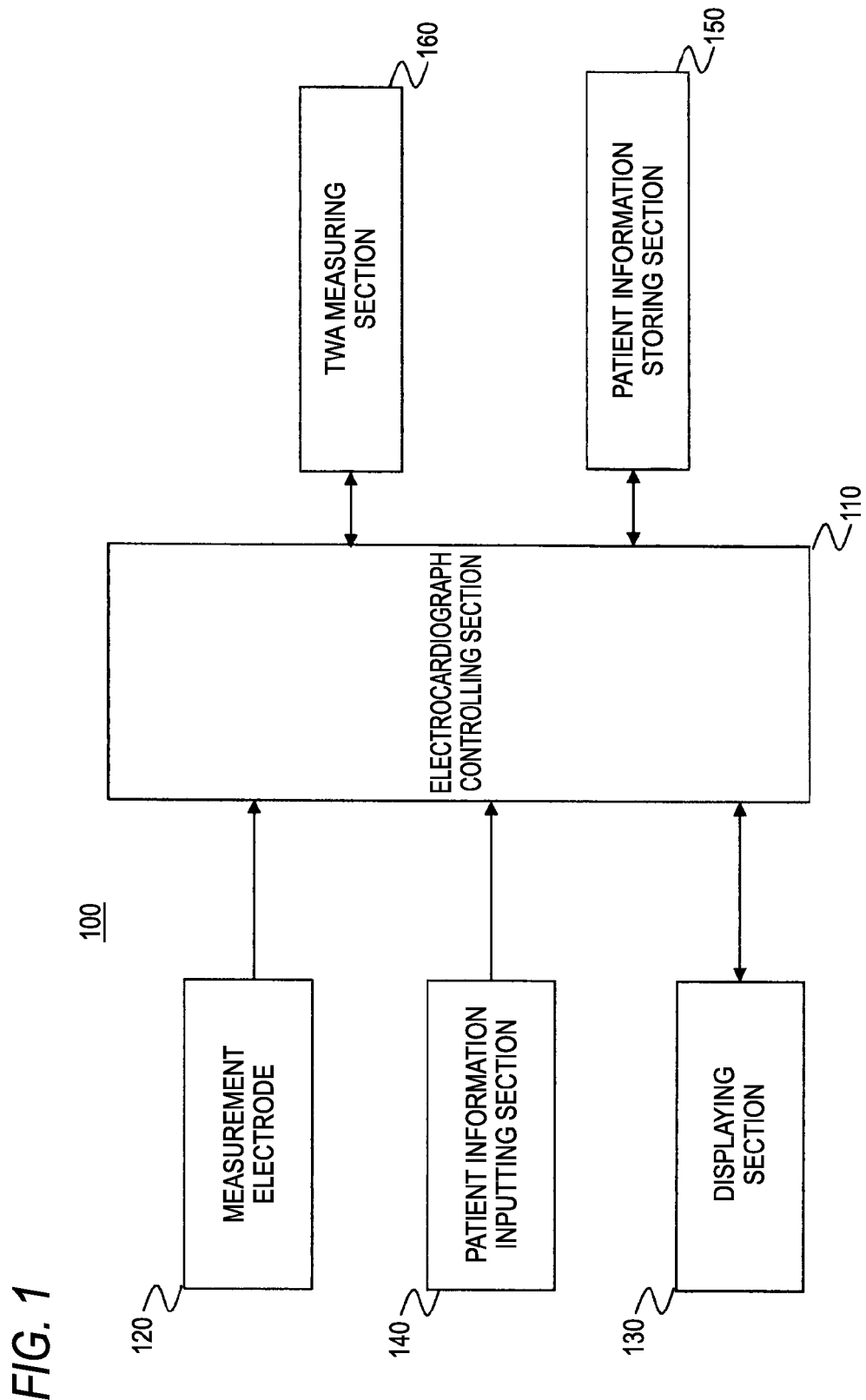
FIG. 1 is a block diagram of TWA measuring apparatuses of Embodiments 1 and 2.

FIG. 1 is a block diagram of the TWA measuring apparatus of Embodiment 1. The TWA measuring apparatus of Embodiment 1 is disposed in an electrocardiogram.

As shown in the figure, the TWA measuring apparatus 100 includes an electrocardiograph controlling section 110, measurement electrodes 120, a displaying section 130, a patient information inputting section 140, a patient information storing section 150, and a TWA measuring section 160.

The electrocardiograph controlling section 110 generally controls the operations of the measurement electrodes 120, the displaying section 130, the patient information inputting section 140, the patient information storing section 150, and the TWA measuring section 160.

The measurement electrodes 120 are electrodes which are to be attached to the body surface of the patient. The number and attachment positions of the used measurement electrodes 120 are different depending on the employed measuring method.

The displaying section 130 displays the electrocardiographic signal which is acquired by the measurement electrodes 120, patient information which is supplied from the patient information inputting section 140, other patient information which is stored in the patient information storing section 150, and a measurement result of the presence of TWA.

The patient information inputting section 140 is used for inputting patient information by means of key operations of the measuring person. The patient information contains a patient ID, the name of the patient, the age of the patient, and the sex of the patient.

The patient information storing section 150 stores the patient information which is input through the patient information inputting section 140, namely, the patient ID, the name of the patient, the age of the patient, and the sex of the patient.

The TWA measuring section 160 measures in detail variations of the heartbeat by using the electrocardiogram waveforms stored in the electrocardiograph controlling section 110, to measure the presence of TWA.

Figure 2:
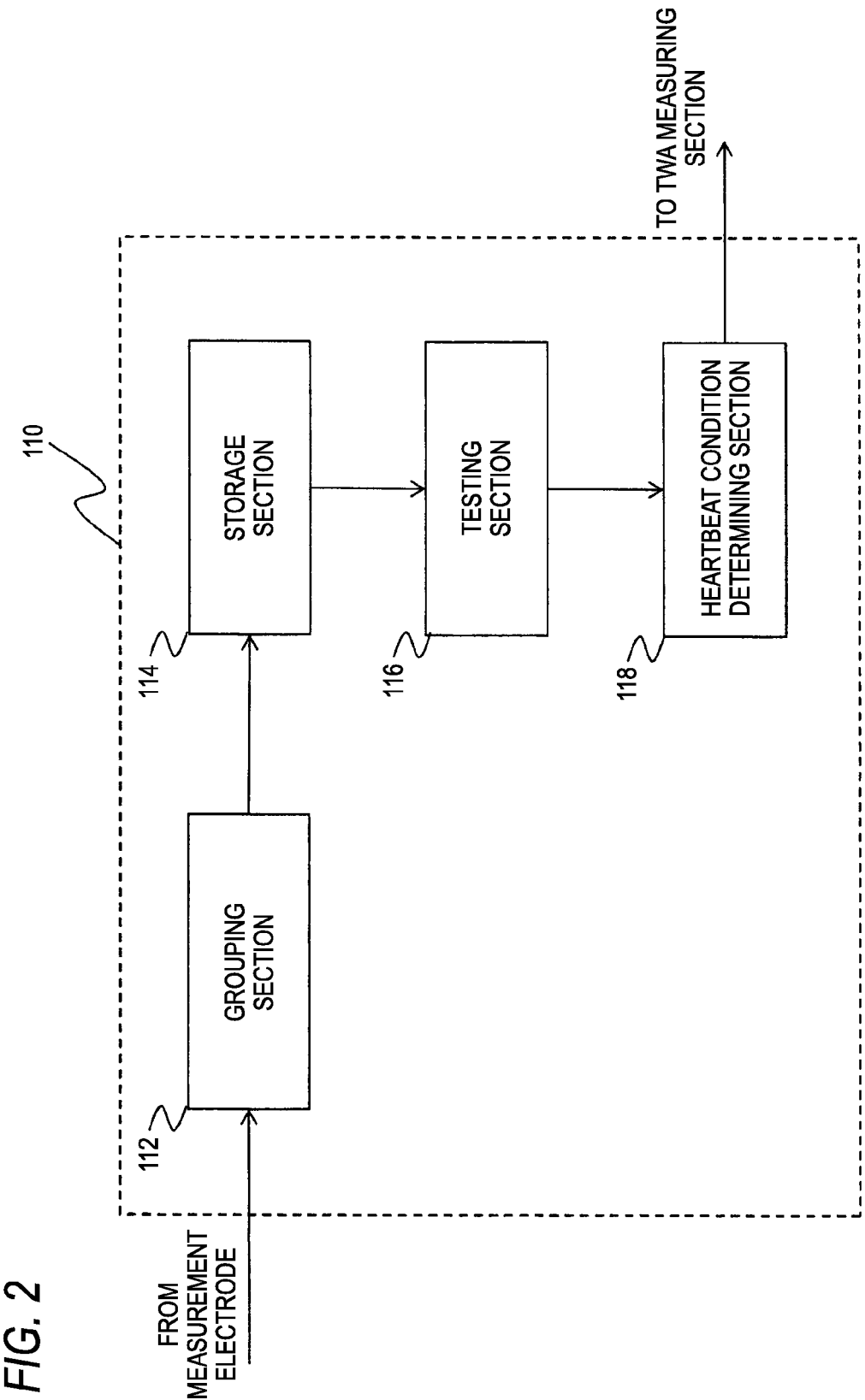
FIG. 2 is a block diagram of an electrocardiograph controlling section in FIG. 1.

FIG. 2 is a block diagram of the electrocardiograph controlling section 110 in FIG. 1.

The electrocardiograph controlling section 110 has a grouping section 112, a storage section 114, a testing section 116, and a heartbeat condition determining section 118.

The grouping section 112 groups the electrocardiogram waveforms acquired by the measurement electrodes 120, in increments of a constant beat number (hereinafter, such an increment is referred to as "constant-beat number increment"). In the embodiment, the constant-beat number increment is set to a 2-beat increment.

Figure 7:
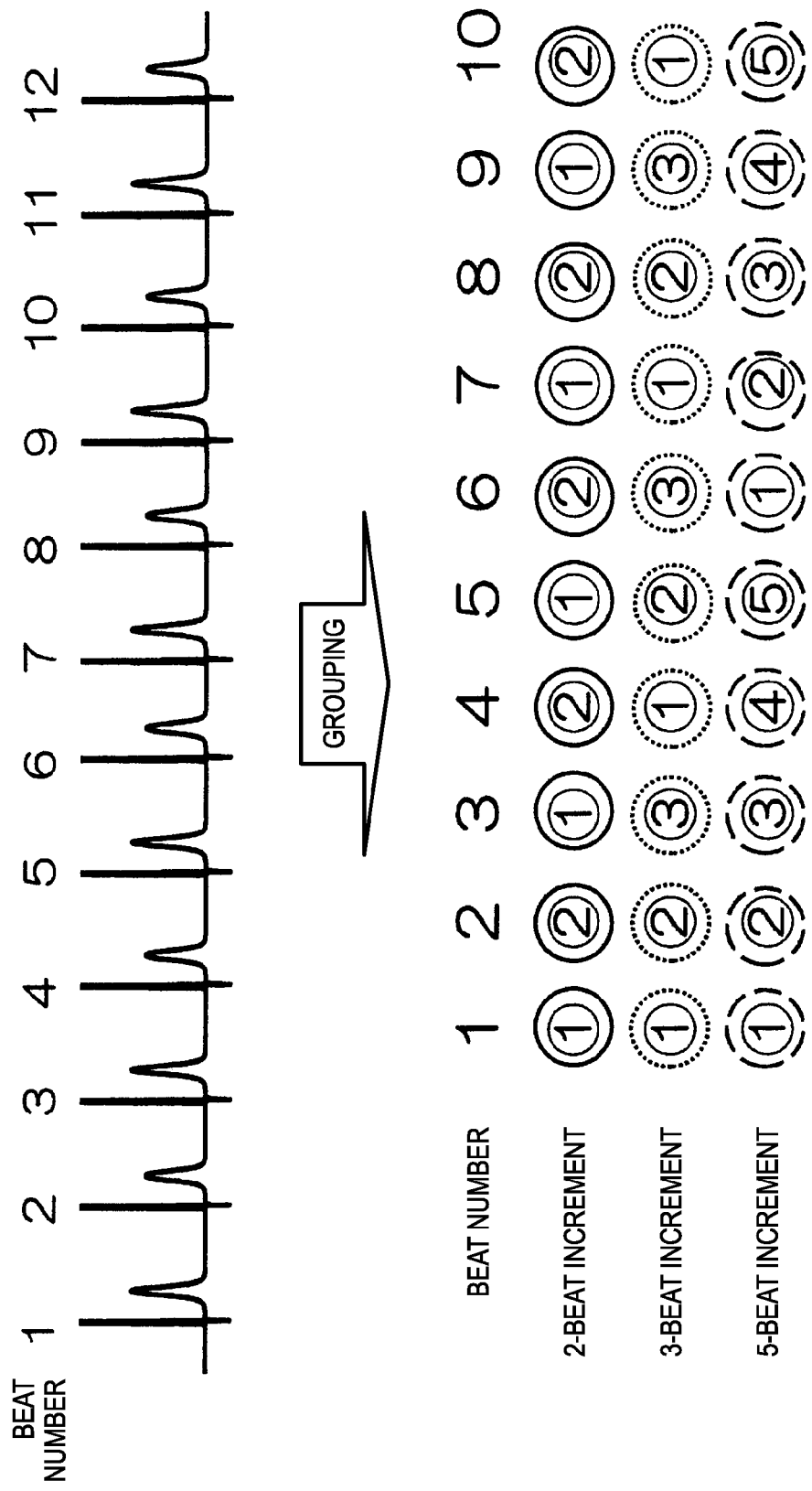
FIG. 7 is a view illustrating a technique for grouping electrocardiogram waveforms in increments of a constant beat number.

As shown in FIG. 7, continuous beat numbers are assigned to the electrocardiogram waveforms acquired by the measurement electrodes 120. In the embodiment, electrocardiogram waveforms of odd beats such as first, third, fifth, . . . beats are grouped as a first group, and those of even beats such as second, fourth, sixth, . . . beats are grouped as a second group. Therefore, electrocardiogram waveforms of odd beats and those of even beats are grouped, and two groups are generated.

In a case where the constant-beat number increment is set to a 3-beat increment, as shown in FIG. 7, electrocardiogram waveforms of first, fourth, seventh, . . . beat numbers are grouped as a first group, those of second, fifth, eighth, . . . beat numbers are grouped as a second group, and those of beat numbers of third, sixth, ninth, . . . beat numbers are grouped as a third group. When the constant-beat number increment is set to a 3-beat increment as described above, therefore, three groups are generated.

In a further case where the constant-beat number increment is set to a 5-beat increment, as shown in FIG. 7, electrocardiogram waveforms of first, sixth, eleventh, . . . beat numbers are grouped as a first group, those of second, seventh, twelfth, . . . beat numbers are grouped as a second group, those of third, eighth, thirteenth, . . . beat numbers are grouped as a third group, those of fourth, ninth, fourteenth, . . . beat numbers are grouped as a fourth group, and those of fifth, tenth, fifteenth, . . . beat numbers are grouped as a fifth group. When the constant-beat number increment is set to a 5-beat increment as described above, therefore, five groups are generated.

The grouping section 112 groups the electrocardiogram waveforms by using electrocardiogram waveforms of a constant beat number. In the grouping section 112, for example, the heartbeat numbers of electrocardiogram waveforms which are to be used in respective cases where grouping is performed in 2-, 3-, and 5-beat increments are set. In the embodiment, grouping is performed by using electrocardiogram waveforms of 100 beats.

In the above-described example where grouping is performed in 2-beat increments, therefore, electrocardiogram waveforms of 50 beats exist in each of the first and second groups.

The heartbeat number of electrocardiogram waveforms which are to be used is determined while comprehensively considering the number of heartbeats in which grouping is to be performed, the required minimum number of heartbeats in the statistical processing, the length of the allowable time for acquiring an electrocardiographic signal, the processing ability of the electrocardiogram, and the like.

In the grouping section 112, as the constant-beat number increment in grouping of electrocardiogram waveforms, an increment of a prime beat number (hereinafter, such an increment is referred to as "prime-beat number increment"), or namely an increment of a positive integer number of beats, the positive integer number not having a divisor other than the number itself and 1 is employed. Specifically, a 2-beat increment, a 3-beat increment, a 5-beat increment, a 7-beat increment, an 11-beat increment, . . . , or the like is employed.

The reason why a prime-beat number increment is employed is that statistical processing is enabled in which the feature of TWA having a phenomenon that the amplitude and polarity of the T-wave alternately change every beat can be well extracted.

The storage section 114 stores the electrocardiogram waveforms which are grouped by the grouping section 112, for each group. As described above, when electrocardiogram waveforms are grouped in 2-beat increments, two groups of electrocardiogram waveforms are stored, and, when electrocardiogram waveforms are grouped in 5-beat increments, five groups of electrocardiogram waveforms are stored.

The testing section 116 tests a statistical intergroup difference of the measurement values of the electrocardiogram waveforms stored in the storage section 114. As the measurement values which are used in the testing of the statistical difference by the testing section 116, at least one of measurement values (measurement information) including the crest value, width, frequency information, correlation, and the like of the electrocardiogram waveforms is employed.

Therefore, the testing section 116 tests whether or not a statistical difference exists between measurement information of electrocardiogram waveforms in the own group and that in the other groups (whether or not there is a possibility that TWA exists), by using a testing method such as the t-test or the analysis of variance.

If, as a result of the testing by the testing section 116, a significant statistical difference exists between the groups, the heartbeat condition determining section 118 determines that the heartbeat condition is unstable (that there is a possibility that TWA exists), and, if a significant difference does not exist, determines that the heartbeat condition is stable (that TWA does not exist).

If the heartbeat condition determining section 118 determines that the heartbeat condition is unstable, the TWA measuring section 160 shown in FIG. 1 measures in detail the variation in heartbeat by using the electrocardiogram waveforms stored in the storage section 114 (irrespective of the groups).

Specifically, the TWA measuring section 160 performs FFT processing on a constant number of electrocardiogram waveforms in the electrocardiogram waveforms stored in the storage section 114 to calculate a periodogram, calculates the alternans value of the electrocardiogram waveforms which have undergone the calculation of a periodogram, and determines the presence of TWA by using the alternans value.

Alternatively, the TWA measuring section 160 extracts a constant number of electrocardiogram waveforms in the electrocardiogram waveforms stored in the storage section 114, produces typical waveforms (average waveforms, median waveforms, or the like) of odd and even beats, and compares the typical waveforms of odd and even beats with each other, thereby determining the presence of TWA. The following description will be made assuming that the typical waveforms are average waveforms.

The operation of the TWA measuring section 160 will be described later in further detail.

(Operation of TWA Measuring Apparatus)

Figure 3:
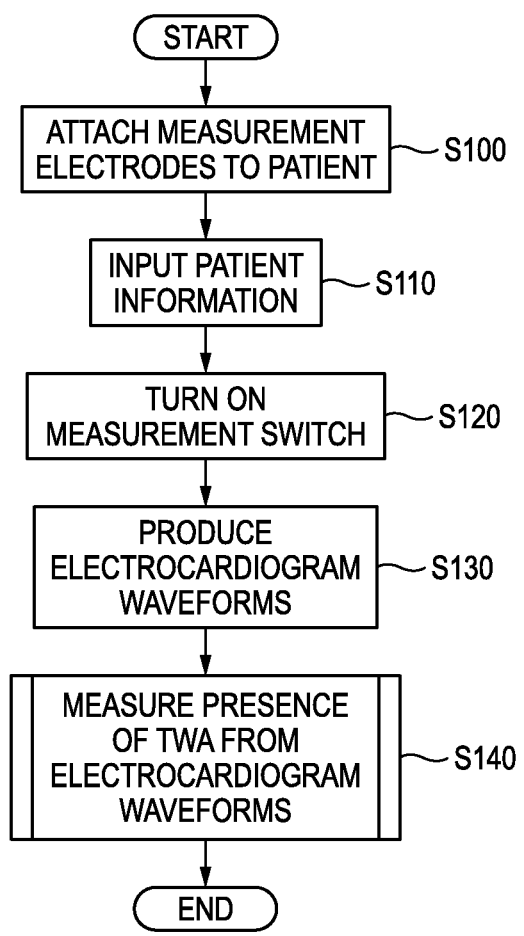
FIG. 3 is an operation flowchart of the TWA measuring apparatuses of Embodiments 1 and 2.

Next, the operation of the TWA measuring apparatus of Embodiment 1 will be described. FIG. 3 is an operation flowchart of the TWA measuring apparatuses of Embodiment 1.

In the operation flowchart of FIG. 3, the operations of steps S100 to S120 are performed by the operator (measuring person) of the TWA measuring apparatus, and the operation of step S130 is performed by the electrocardiograph controlling section 110 and the TWA measuring section 160. The operations of steps S100 to S140 correspond also to the procedure of the TWA measuring method of Embodiment 1.

<Step S100>

The operator of the TWA measuring apparatus 100 (electrocardiograph) shown in FIG. 1 attaches the measurement electrodes 120 to predetermined portions of the body surface of the patient. Since the TWA measuring apparatus 100 of Embodiment 1 targets electrocardiograms which are produced by various measuring methods, the measurement electrodes 120 are attached respectively to measurement portions of the patient which are determined in the employed measuring method.

In the case where a derived 12-lead electrocardiogram is to be produced, for example, the measurement electrodes 120 are attached to a total of ten places, i.e., four places or the right and left arms (electrodes L, R) and the right and left lower limbs (electrodes LL, RL) in order to acquire electrocardiographic signals of four limb leads (lead I, lead II, lead III, lead aVR, lead aVL, and lead aVF), and the lower right sternal edge of the fourth intercostal space (lead V1), the lower left sternal edge of the fourth intercostal space (lead V2), the fifth intercostal space in the midclavicular line (lead V4), the midpoint between leads V2 and V4 (lead V3), the left anterior axillary line at the height of V4 (lead V5), and the left middle axillary line at the height of V4 (lead V6) in order to acquire electrocardiographic signals of chest leads (lead V1, lead V2, lead V3, lead V4, lead V5, and lead V6).

<Step S110>

Next, the operator inputs patient information through the patient information inputting section 140. For example, the patient ID, the name of the patient, the age of the patient, and the sex of the patient are input. The input patient information is stored in the patient information storing section 150. The electrocardiogram waveforms which are acquired by the measurement electrodes 120 in the subsequent steps are tagged with the patient information.

<Step S120>

Then, the operator turns ON a measurement switch (not shown) of the TWA measuring electrocardiograph 100. When the measurement switch is turned ON, the measurement of the presence of TWA is started.

<Step S130>

The electrocardiograph controlling section 110 produces electrocardiogram waveforms from electrocardiographic signals of the measurement electrodes 120 which are attached in step S100 to the patient. The electrocardiograph controlling section 110 produces electrocardiogram waveforms by a technique according to the employed measuring method. For example, the electrocardiogram waveforms are produced from the electrocardiographic signal which is acquired by a measuring method such as a Frank's vector electrocardiogram, and a usual scalar electrocardiogram, i.e., a standard 12-lead electrocardiogram, a derived lead electrocardiogram, a Holter electrocardiogram, an event electrocardiogram, an exercise electrocardiogram, and a monitoring electrocardiogram, by the technique according to the measuring method.

The TWA measuring section 160 measures the presence of TWA from the acquired electrocardiogram waveforms. The process of the step will be specifically described with reference to the flowcharts of FIGS. 4 to 6.

Figure 4:
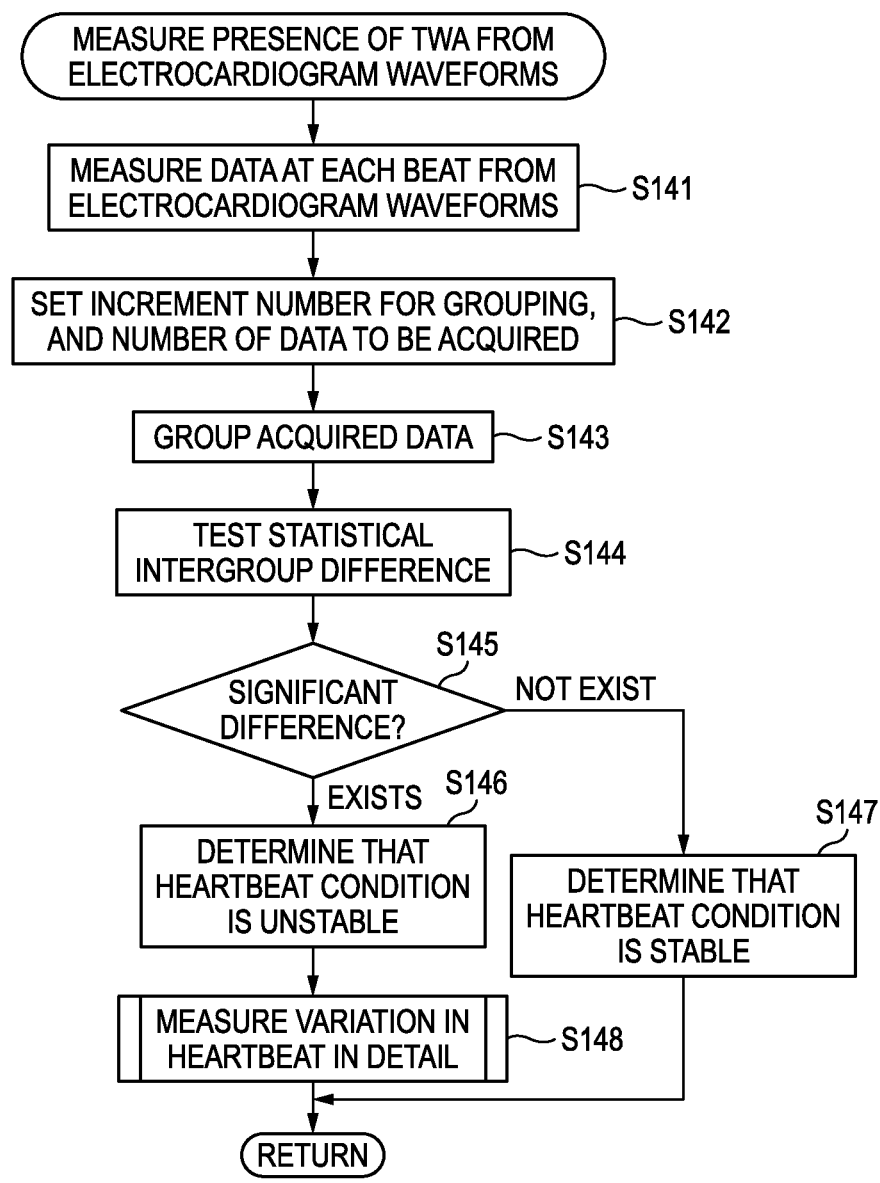
FIG. 4 is a subroutine flowchart of step S140 in the operation flowchart of FIG. 3 (this is applied to Embodiments 1 and 3).

FIG. 4 is a subroutine flowchart of step S140 in the operation flowchart of FIG. 3.

<Step S141>

The electrocardiograph controlling section 110 receives the electrocardiogram waveforms acquired by the measurement electrodes 120, beat by beat, and measures measurement information of the received electrocardiogram waveforms.

<Step S142>

The increment number for grouping the electrocardiogram waveforms acquired by the measurement electrodes 120, and the number of data to be acquired are set in the grouping section 112. These numbers are previously set in the grouping section 112. The number of increments is set by using prime numbers as described above. The number of data to be acquired coincides with that of the electrocardiogram waveforms which are to be used in the grouping.

<Step S143>

The grouping section 112 groups the electrocardiogram waveforms acquired by the measurement electrodes 120, in constant-beat number increments.

For example, it is assumed that, in the grouping section 112, 2 is set as the number of increments, and 100 is set as that of data to be acquired. The grouping section 112 performs grouping so that the data (measurement information of the electrocardiogram waveforms) acquired from the electrocardiogram waveform of the first beat belong to the first group, those acquired from the electrocardiogram waveform of the second beat belong to the second group, those acquired from the electrocardiogram waveform of the third beat belong to the first group, those acquired from the electrocardiogram waveform of the fourth beat belong to the second group, . . . . This grouping is performed on the first to hundredth beat numbers.

Therefore, 50 numbers of data acquired from the electrocardiogram waveforms of odd beats constitute the first group, and 50 numbers of data acquired from those of even beats constitute the second group.

The data of the electrocardiogram waveforms which have been grouped by the grouping section 112 are stored in the storage section 114.

<Step S144>

The testing section 116 extracts the data of the first group, and those of the second group which are stored in the storage section 114, and tests a statistical intergroup difference of data of electrocardiogram waveforms (measurement information of the electrocardiogram waveforms) of the groups.

In the case of electrocardiogram waveforms containing TWA, for example, it is seen that, as shown in FIG. 7, the amplitudes of T waves of electrocardiogram waveforms of odd beats are larger than those of T waves of electrocardiogram waveforms of even beats. Therefore, it is expected that electrocardiogram waveform data of the first group configured by 50 data acquired from the electrocardiogram waveforms of odd beats are obviously statistically different from those of the second group configured by 50 data acquired from the electrocardiogram waveforms of even beats. The testing section 116 tests the statistical difference between the first and second groups by using a testing method such as the t-test or the analysis of variance.

<Step S145>

The heartbeat condition determining section 118 determines whether a significant statistical difference exists between the groups tested by the testing section 116 or not (whether or not there is a possibility that TWA exists). In the case where the acquired electrocardiographic signals contain TWA, as described above, the electrocardiogram waveform data of the first group are different from those of the second group. If the possibility that the difference occurs by chance is included in the rejection region, a significant statistical difference exists between the groups, and, if not included, a significant statistical difference does not exist between the groups.

<Step S146>

When the heartbeat condition determining section 118 determines that a significant statistical difference exists between the groups, the possibility that TWA is contained in the acquired electrocardiographic signals is high, and therefore the heartbeat condition determining section 118 determines that the heartbeat condition is unstable.

<Step S147>

When the heartbeat condition determining section 118 determines that a significant statistical difference does not exist between the groups, the possibility that TWA is contained in the acquired electrocardiographic signals is low, and therefore the heartbeat condition determining section 118 determines that the heartbeat condition is stable.

<Step S148>

When the heartbeat condition determining section 118 determines that the heartbeat condition is unstable, the possibility that TWA is contained in the acquired electrocardiographic signals is high, and therefore the TWA measuring section 160 measures the variation in heartbeat (the magnitude of TWA) in detail by using the electrocardiogram waveforms stored in the storage section 114. The process of the step will be specifically described with reference to the operation flowchart of FIG. 5.

Figure 5:
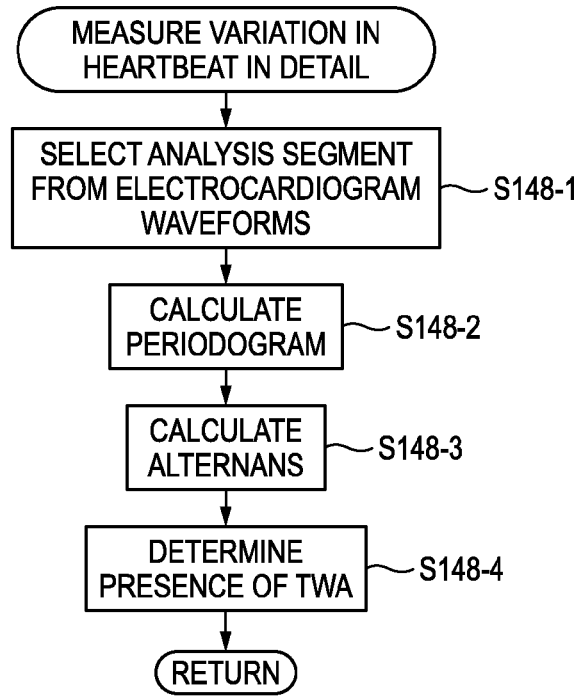
FIG. 5 is a subroutine flowchart of step S148 in the subroutine flowchart of FIG. 4 (this is applied to Embodiments 1 to 4).

FIG. 5 is a subroutine flowchart of step S148 in the subroutine flowchart of FIG. 4.

<Step S148-1>

The TWA measuring section 160 selects electrocardiogram waveforms of 128 or more beats, for example, 150 beats from the electrocardiogram waveforms stored in the storage section 114. There is a possibility that, in the selected electrocardiogram waveforms of 150 beats, waveforms which are largely different in shape may be included. Therefore, the waveforms of 128 beats in which correlations between the electrocardiogram waveforms are equal to or larger than a given threshold are selected from the selected electrocardiogram waveforms of 150 beats.

Specifically, first, an average waveform which is obtained by averaging the electrocardiogram waveforms of 150 beats in a first designated time period is obtained. Then, waveforms of 128 beats in which the correlations between the respective waveforms and the average waveform are equal to or larger than the given threshold are determined.

Then, ST-T segments of the thus selected electrocardiogram waveforms of 128 beats are selected as an analysis segment.

<Step S148-2>

Figure 8:
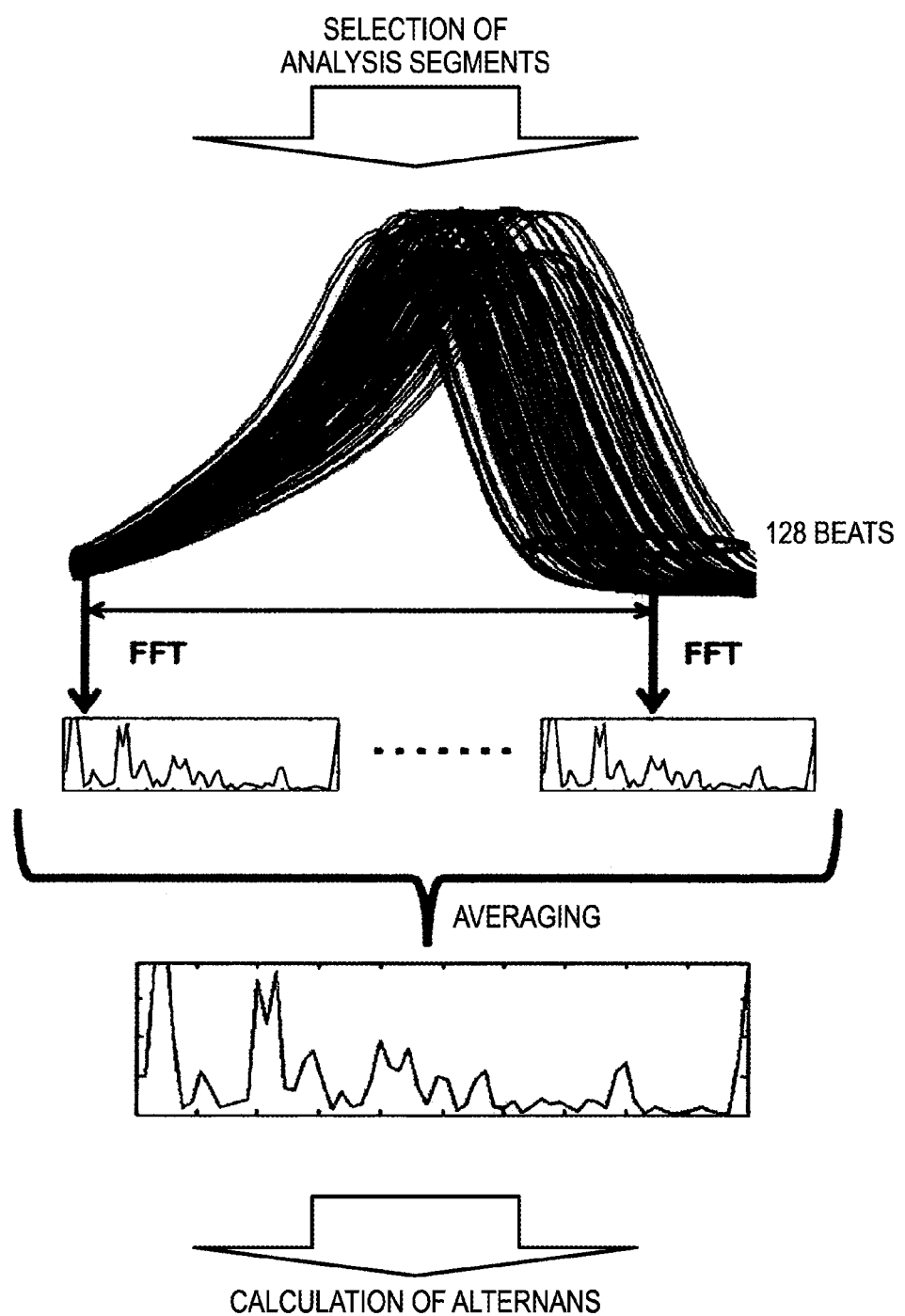
FIG. 8 is a view illustrating a process of selecting an analysis segment.

As shown in FIG. 8, the TWA measuring section 160 performs the FFT process on the analysis segment of 128 beats, and calculates a periodogram.

Figure 9:
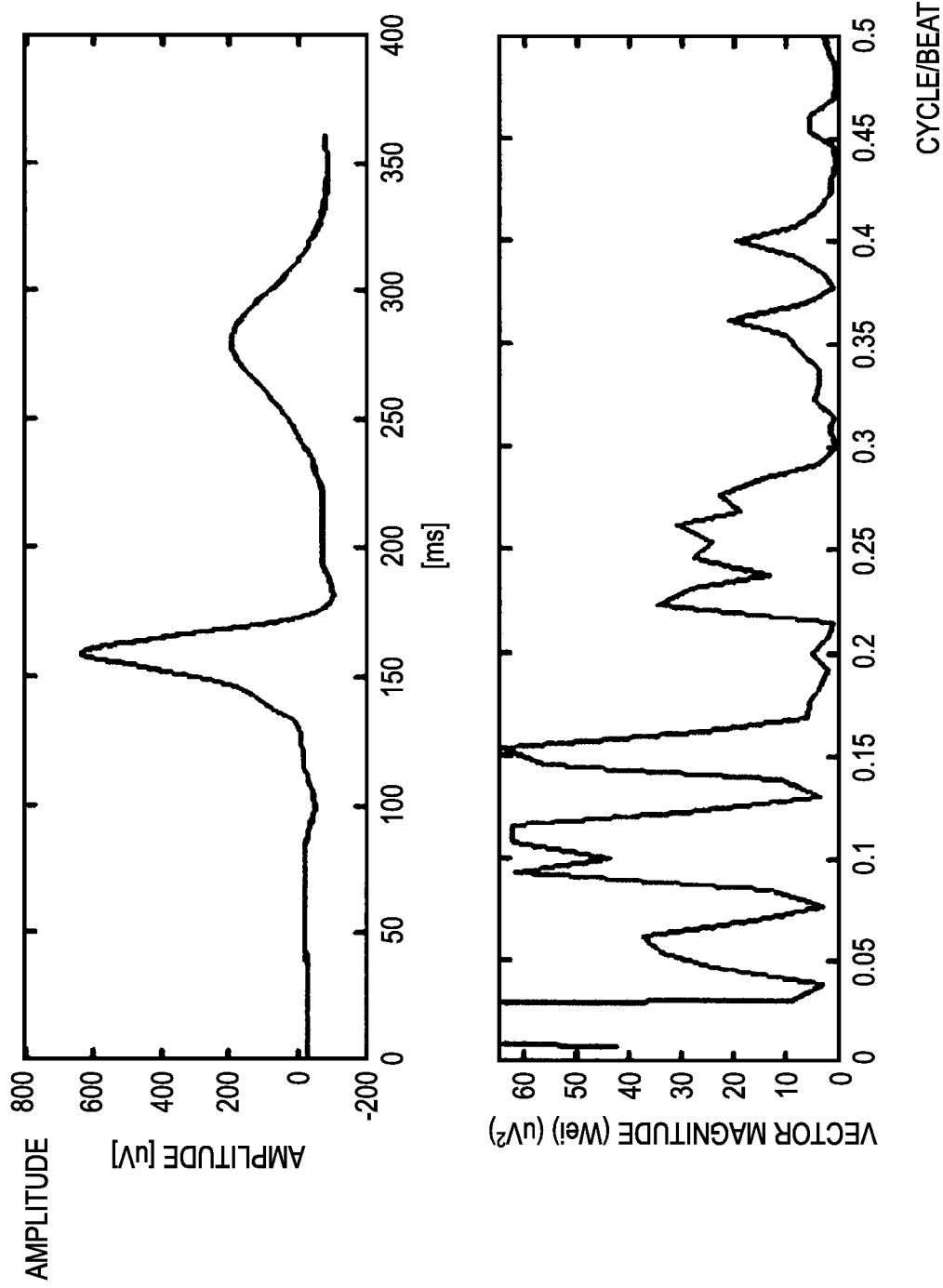
FIG. 9 is a view illustrating a process of calculating a periodogram.
Figure 10:
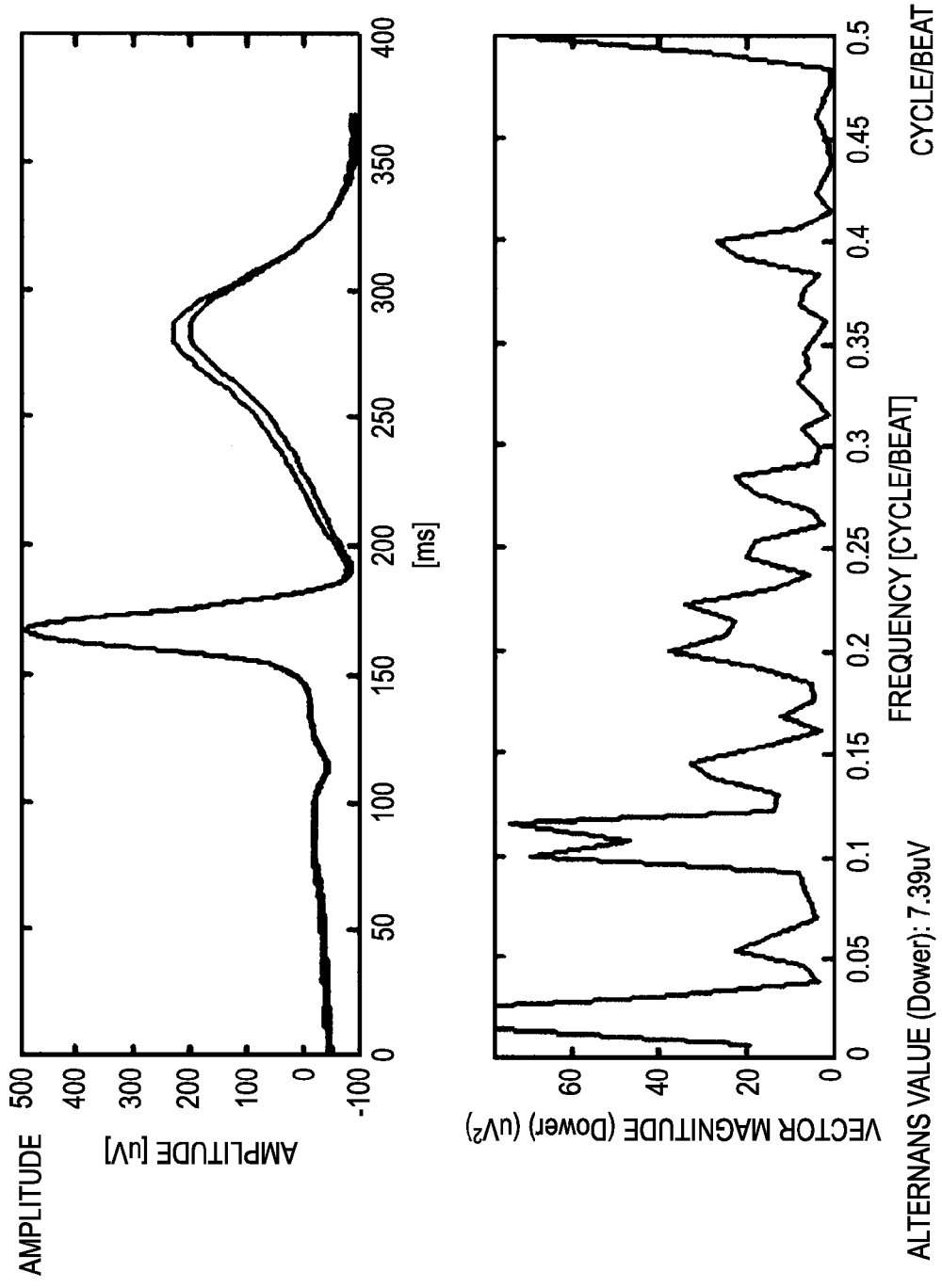
FIG. 10 is a view illustrating the process of calculating a periodogram.

FIGS. 9 and 10 are views for illustrating a periodogram. The upper waveform charts of FIGS. 9 and 10 show average waveforms of odd and even beats, respectively. The lower waveform charts of FIGS. 9 and 10 show waveforms which are obtained after a periodogram is calculated.

The waveform of FIG. 9 which is obtained after a periodogram is calculated shows that, when the frequency (cycle/beat) is 0.5, the value of the vector magnitude is small. This means that there is no TWA. By contrast, the waveform of FIG. 10 which is obtained after a periodogram is calculated shows that, when the frequency (cycle/beat) is 0.5, the value of the vector magnitude is large. This means that the value of TWA is large, and the possibility that TWA exists is large.

As described above, when a periodogram is calculated, the presence of TWA can be predicted to some extent from the magnitude of the value of the vector magnitude.

<Step S148-3>

Next, the TWA measuring section 160 calculates alternans. In the waveform charts which are shown in FIGS. 9 and 10, and which are obtained after a periodogram is calculated, the zone where the cycle/beat frequency is from 0.44 to 0.49 is defined as a noise band, and the average $S_{NB}$ and standard deviation $\sigma_{NB}$ of the zone are obtained. The value which is obtained when the cycle/beat frequency is 0.5 is indicated by $S_{0.5}$, and the following Formula 1 is calculated, thereby calculating alternans $V_{alt}$.

$$V_{alt} = (S_{0.5} - S_{NB})^{1/2} \qquad \text{Formula 1}$$

<Step S148-4>

The TWA measuring section 160 determines the presence of TWA. By using the average $S_{NB}$ of the zone and value of alternans $V_{alt}$ which are calculated in step S148-3, the following Formula 2 is calculated, thereby calculating an alternans ratio k.

$$k = (V_{alt})^2 / \sigma_{NB} \quad \text{Formula 2}$$

Then, the presence of TWA is determined from the values of the alternans $V_{alt}$ and the alternans ratio k. Conditions for determining the presence of TWA are the alternans $V_{alt} > 1.9$ μV and the alternans ratio $k > 3$. When the determination conditions are satisfied, it is determined that TWA exists.

As described above, when the shapes of the acquired electrocardiogram waveforms are analyzed, it is possible to determine the presence of TWA in which T waves having different shapes appear alternately at each beat (ABABAB . . . ).

(Other Operation of TWA Measuring Section)

In the above-described TWA measuring apparatus 100, the TWA measuring section 160 obtains a periodogram and an alternans, and measures in detail the variation in heartbeat from the electrocardiogram waveforms stored in the storage section 114. In the following, a process in a modification of Embodiment 1 is shown in which the variation in heartbeat is measured in detail by performing a process that is different from that described above.

Figure 6:
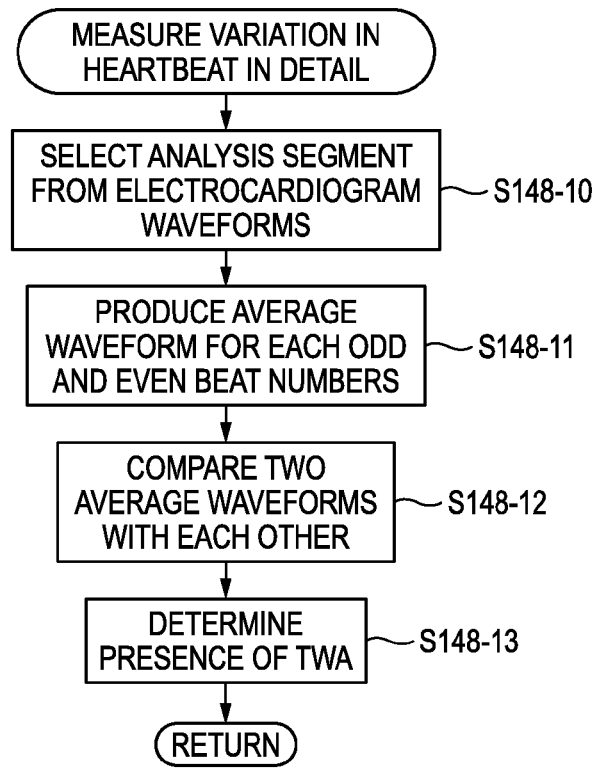
FIG. 6 is a subroutine flowchart showing another process of step S148 in the subroutine flowchart of FIG. 4 (this is applied to modifications of Embodiments 1 to 4).

FIG. 6 is a subroutine flowchart showing another process of step S148 in the subroutine flowchart of FIG. 4.

<Step S148-10>

The TWA measuring section 160 selects electrocardiogram waveforms of 128 or more beats, for example, 150 beats from the electrocardiogram waveforms stored in the storage section 114. There is a possibility that, in the selected electrocardiogram waveforms of 150 beats, waveforms which are largely different in shape may be included. Therefore, the waveforms of 128 beats in which correlations between the electrocardiogram waveforms are equal to or larger than a given threshold are selected from the selected electrocardiogram waveforms of 150 beats.

Specifically, first, an average waveform which is obtained by averaging the electrocardiogram waveforms of 150 beats in a first designated time period is obtained. Then, waveforms of 128 beats in which the correlations between the respective waveforms and the average waveform are equal to or larger than the given threshold are determined.

Then, ST-T segments of the thus selected electrocardiogram waveforms of 128 beats are selected as an analysis segment.

<Step S148-11>

Next, the TWA measuring section 160 divides the analysis segments for 128 beats into segments of odd beat numbers, and those of even beat numbers, and calculates the averages of the odd- and even-beat analysis segments to form average waveforms.

<Step S148-12>

The TWA measuring section 160 compares the odd-beat average waveform with the even-beat average waveform. This is performed because, when there is a large difference between the average waveforms, the possibility that TWA is produced is high.

<Step S148-13>

The TWA measuring section 160 determines the presence of TWA. If the shape difference between the average waveform of odd beats and that of even-beats which is obtained in step S148-12 exceeds a given value, it is determined that TWA is produced.

In Embodiment 1, unlike the related art where the presence of TWA is determined by referring to the value indicative of the reliability of the measurement of TWA, as described above, the acquired electrocardiogram waveforms are grouped in increments of a beat number, and it is determined whether a significant statistical difference exists between the groups or not, thereby determining the presence of TWA. In Embodiment 1, since the statistical analysis is employed, it is possible to determine the presence of TWA with a statistical back-up due to actually acquired electrocardiogram waveforms, without being affected by the value indicative of the reliability of the measurement of TWA which depends on experimental results.

Embodiment 2

Hereinafter, a TWA measuring apparatus and TWA measuring method of Embodiment 2 will be described. In the embodiment, electrocardiogram waveforms acquired by measurement electrodes of an electrocardiogram are divided into two groups in increments of two beats, and three groups in increments of three beats. Then, a statistical intergroup difference of measurement values are tested for each of the beat numbers, and the mixing situation of the presence of a significant statistical difference is checked to determine the presence of TWA.

(Configuration of TWA Measuring Apparatus)

The configuration of the TWA measuring apparatus of Embodiment 2 is identical with that shown in FIGS. 1 and 2. However, only the grouping section 112, testing section 116, and heartbeat condition determining section 118 of the electrocardiograph controlling section 110 are different in function from those in Embodiment 1.

The grouping section 112 groups the electrocardiogram waveforms acquired by the measurement electrodes 120, in increments of the same beat number (hereinafter, such an increment is referred to as "same-beat number increment") for each of a plurality of increments of different beat numbers (hereinafter, such an increment is referred to as "different-beat number increment"). In the embodiment, the plurality of different-beat number increments used in the grouping by the grouping section 112 are a plurality of increments of different prime beat numbers.

In the embodiment, as the plurality of different-beat number increments, two different-beat number increments, i.e., a 2-beat increment and a 3-beat increment are set. In the case where two different-beat number increments of a 2-beat increment and a 3-beat increment are set, the grouping is performed in the following manner.

As shown in FIG. 7, continuous beat numbers are assigned to the electrocardiogram waveforms acquired by the measurement electrodes 120. In the embodiment, electrocardiogram waveforms of odd beats such as first, third, fifth, . . . beats are grouped as a first group of a 2-beat increment, and those of even beats such as second, fourth, sixth, . . . beats are grouped as a second group of a 2-beat increment.

As groups of a same-beat number increment, therefore, electrocardiogram waveforms of a 2-beat increment are grouped into two groups.

As shown in FIG. 7, furthermore, electrocardiogram waveforms of first, fourth, seventh, . . . beat numbers are grouped as a first group of a 3-beat increment, those of second, fifth, eighth, . . . beat numbers are grouped as a second group of a 3-beat increment, and those of beat numbers of third, sixth, ninth, . . . beat numbers are grouped as a third group of a 3-beat increment.

As groups of a same-beat number increment, therefore, electrocardiogram waveforms of a 3-beat increment are grouped into three groups.

The testing section 116 tests a statistical intergroup difference of the data (measurement information of electrocardiogram waveforms) of the electrocardiogram waveforms of the groups of a same-beat number increment stored in the storage section 114. As the measurement values of electrocardiogram waveforms which are used in the testing of the statistical difference by the testing section 116, measurement values is employed similarly with Embodiment 1. In the case of the embodiment, the testing section 116 tests whether or not a statistical difference relating to measurement values of electrocardiogram waveforms exists between the first and second groups of a 2-beat increment, and whether or not a statistical difference relating to measurement values of electrocardiogram waveforms exists between the first, second, and third groups of a 3-beat increment, by using a testing method such as the t-test or the analysis of variance.

The heartbeat condition determining section 118 determines, for each of the plurality of different-beat number increments, whether, as a result of the testing by the testing section 116, a significant statistical difference exists between the groups of a same-beat number increment or not. If it is determined that a significant difference exists for all of the plurality of different-beat number increments, the section determines that it is difficult to evaluate the heartbeat condition. If it is determined that a significant difference does not exist for all of the increments, the section determines that the heartbeat condition is stable. If increments where a significant difference exists, and those where a significant difference does not exist are mixed, the section determines that the heartbeat condition is unstable (that there is a possibility that TWA exists).

Namely, the heartbeat condition determining section 118 determines whether a significant statistical difference exists between the first and second groups of a 2-beat increment or not, and also whether a significant statistical difference exists between the first, second, and third groups of a 3-beat increment or not. If the section determines that a significant difference exists with respect to all of the intergroups between the first and second groups of a 2-beat increment, and between the first, second, and third groups of a 3-beat increment, it is determined that it is difficult to evaluate the heartbeat condition. If the section determines that a significant difference does not exist with respect to all of the intergroups, it is determined that the heartbeat condition is stable. If intergroups where a significant difference exists, and those where a significant difference does not exist are mixed, it is determined that the heartbeat condition is unstable (that there is a possibility that TWA exists).

(Operation of TWA Measuring Apparatus)

Next, the operation of the TWA measuring apparatus of Embodiment 2 will be described. The TWA measuring apparatus of Embodiment 2 is identical in operation with Embodiment 1 except the operation of step S140 of the operation flowchart of FIG. 3 showing the operation of Embodiment 1.

Figure 11:
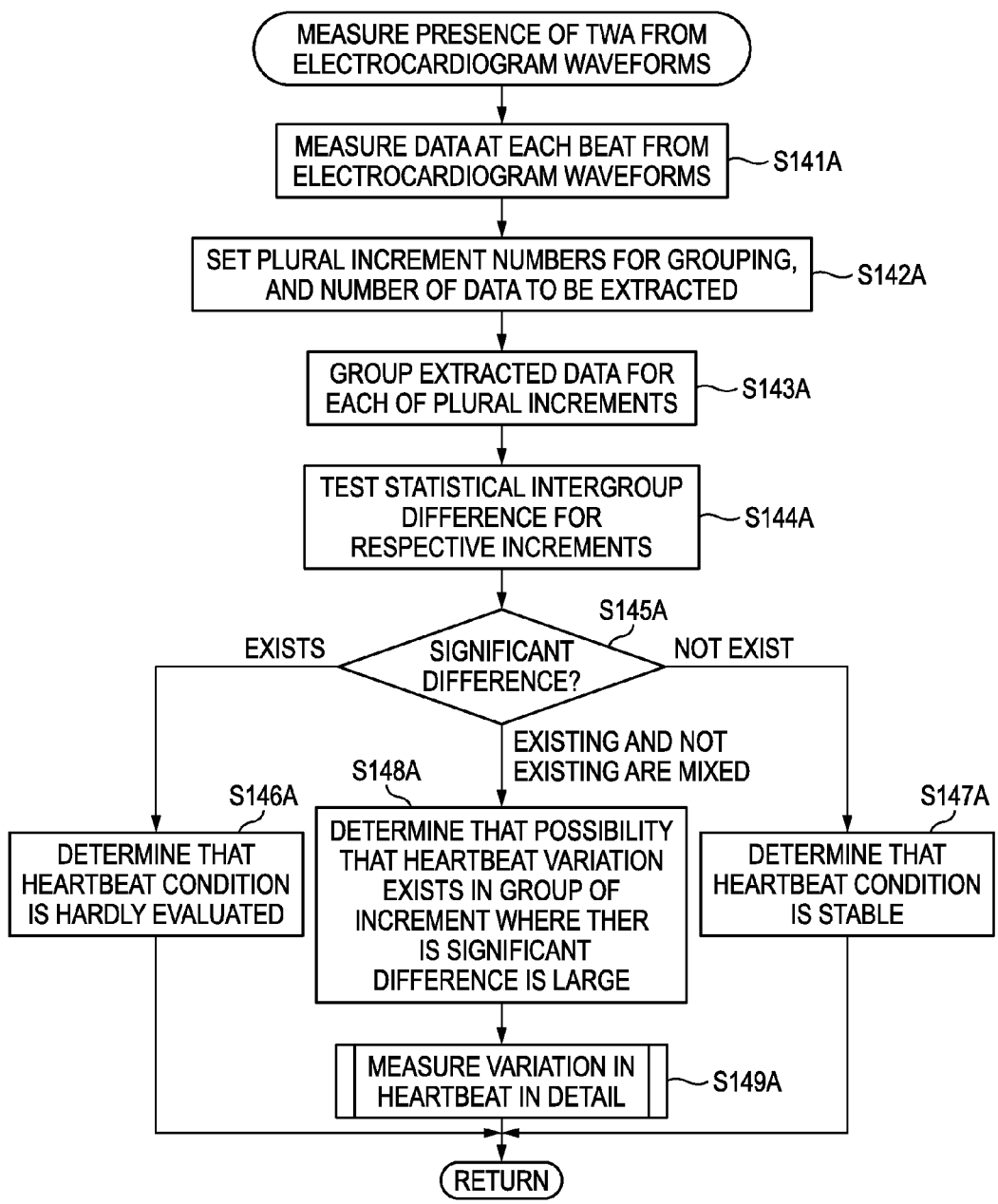
FIG. 11 is a subroutine flowchart of step S140 in the operation flowchart of FIG. 3 (this is applied to Embodiments 2 and 4).

With respect to the operation of the TWA measuring apparatus of Embodiment 2, therefore, only the subroutine flowchart of FIG. 11 will be described.

<Step S141A>

The electrocardiograph controlling section 110 receives the electrocardiogram waveforms acquired by the measurement electrodes 120, beat by beat, and measures measurement information of the received electrocardiogram waveforms.

<Step S142A>

The different increment numbers for grouping the electrocardiogram waveforms acquired by the measurement electrodes 120, and the number of data to be acquired are set in the grouping section 112. These numbers are previously set in the grouping section 112. The number of increments is set by using prime numbers as described above. The number of data to be acquired coincides with that of the electrocardiogram waveforms which are to be used in the grouping. In the embodiment, for example, a 2-beat increment and a 3-beat increment are set as the different increment numbers, and 100 is set as the number of data to be acquired.

<Step S143A>

The grouping section 112 groups data of electrocardiogram waveforms acquired by the measurement electrodes 120, in same-beat number increments for each of the plurality of different-beat number increments.

For example, it is assumed that, in the grouping section 112, 2 and 3 are set as the increment numbers, and 100 is set as the number of data to be acquired.

The grouping section 112 performs grouping so that data (measurement information of the electrocardiogram waveforms) acquired from the electrocardiogram waveform of the first beat belong to the first group of a 2-beat increment, those of the second beat belong to the second group of a 2-beat increment, those of the third beat belong to the first group of a 2-beat increment, those of the fourth beat belong to the second group of a 2-beat increment, . . . . This grouping is performed on the first to hundredth beat numbers.

Moreover, the grouping section 112 performs grouping so that data (measurement information of the electrocardiogram waveforms) acquired from the electrocardiogram waveform of the first beat belong to the first group of a 3-beat increment, those of the second beat belong to the second group of a 3-beat increment, those of the third beat belong to the third group of a 3-beat increment, those of the fourth beat belong to the first group of a 3-beat increment, those of the fifth beat belong to the second group of a 3-beat increment, those of the sixth beat belong to the third group of a 3-beat increment, . . . . This grouping is performed on the first to hundredth beat numbers.

Therefore, the first and second groups are produced as groups of a 2-beat increment, and the first, second, and third groups are produced as groups of a 3-beat increment.

The data of the electrocardiogram waveforms which have been grouped by the grouping section 112 are stored in the storage section 114.

<Step S144A>

The testing section 116 extracts the data of the first and second groups of a 2-beat increment, and those of the first, second, and third groups of a 3-beat increment which are stored in the storage section 114, and tests a statistical difference of measurement values between the groups of the respective beat increments.

Specifically, a statistical difference between the first and second groups of a 2-beat increment is tested by using a testing method such as the t-test or the analysis of variance. Furthermore, a statistical difference between the first, second, and third groups of a 3-beat increment is tested by using a testing method such as the t-test or the analysis of variance.

<Step S145A>

The heartbeat condition determining section 118 determines whether a significant statistical difference exists between the groups of the respective beat increments tested by the testing section 116 or not.

Specifically, it is determined whether a significant statistical difference exists between the first and second groups of a 2-beat increment or not, and whether a significant statistical difference exists between the first, second, and third groups of a 3-beat increment or not.

In the case where the acquired electrocardiographic signals contain TWA, as described above, the electrocardiogram waveform data of the groups are different from each other. If the possibility that the difference occurs by chance is included in the rejection region, a significant statistical difference exists between the groups, and, if not included, a significant statistical difference does not exist between the groups.

<Step S146A>

When the heartbeat condition determining section 118 determines that a significant statistical difference exists with respect to all of the intergroups between the groups of a same-beat number increment, there is the possibility that TWA is contained in the acquired electrocardiographic signals, but it is determined that the heartbeat condition is hardly evaluated.

<Step S147A>

When the heartbeat condition determining section 118 determines that a significant statistical difference does not exist with respect to all of the intergroups between the groups of a same-beat number increment, the possibility that TWA is contained in the acquired electrocardiographic signals is low, and therefore the heartbeat condition determining section 118 determines that the heartbeat condition is stable.

<Step S148A>

If intergroups where a significant difference exists, and those where a significant difference does not exist are mixed between the groups of a same-beat number increment, the heartbeat condition determining section 118 determines that there is the possibility that TWA is contained in the acquired electrocardiographic signals.

<Step S149A>

The TWA measuring section 160 measures in detail the variation in heartbeat by using the electrocardiogram waveforms stored in the storage section 114. The specific process of the step is identical with the processes of the flowcharts of FIGS. 4 and 6 which have been described in Embodiment 1.

Embodiment 3

Hereinafter, a TWA measuring apparatus and TWA measuring method of Embodiment 3 will be described. In the embodiment, an electrocardiogram data inputting section is disposed in place of the measurement electrodes 120 in Embodiment 1. The processes performed until when, based on the acquired electrocardiogram waveforms, it is determined whether the presence of TWA exists or not are identical with those of Embodiment 1. Namely, the processes which are identical with the processes shown in the flowcharts of FIGS. 3 to 6 are performed.

Although the TWA measuring apparatus of Embodiment 1 is disposed in the electrocardiograph, that of the embodiment is disposed in a computer instead of the electrocardiograph. The embodiment is employed in the case where, as in an electrocardiogram such as a Holter electrocardiogram or a monitoring electrocardiogram, data are collected for a long time period, and downloaded into the computer to be used in determining whether TWA exists or not.

The configuration and operation of the TWA measuring apparatus of the embodiment will be briefly described.

(Configuration of TWA Measuring Apparatus)

Figure 12:
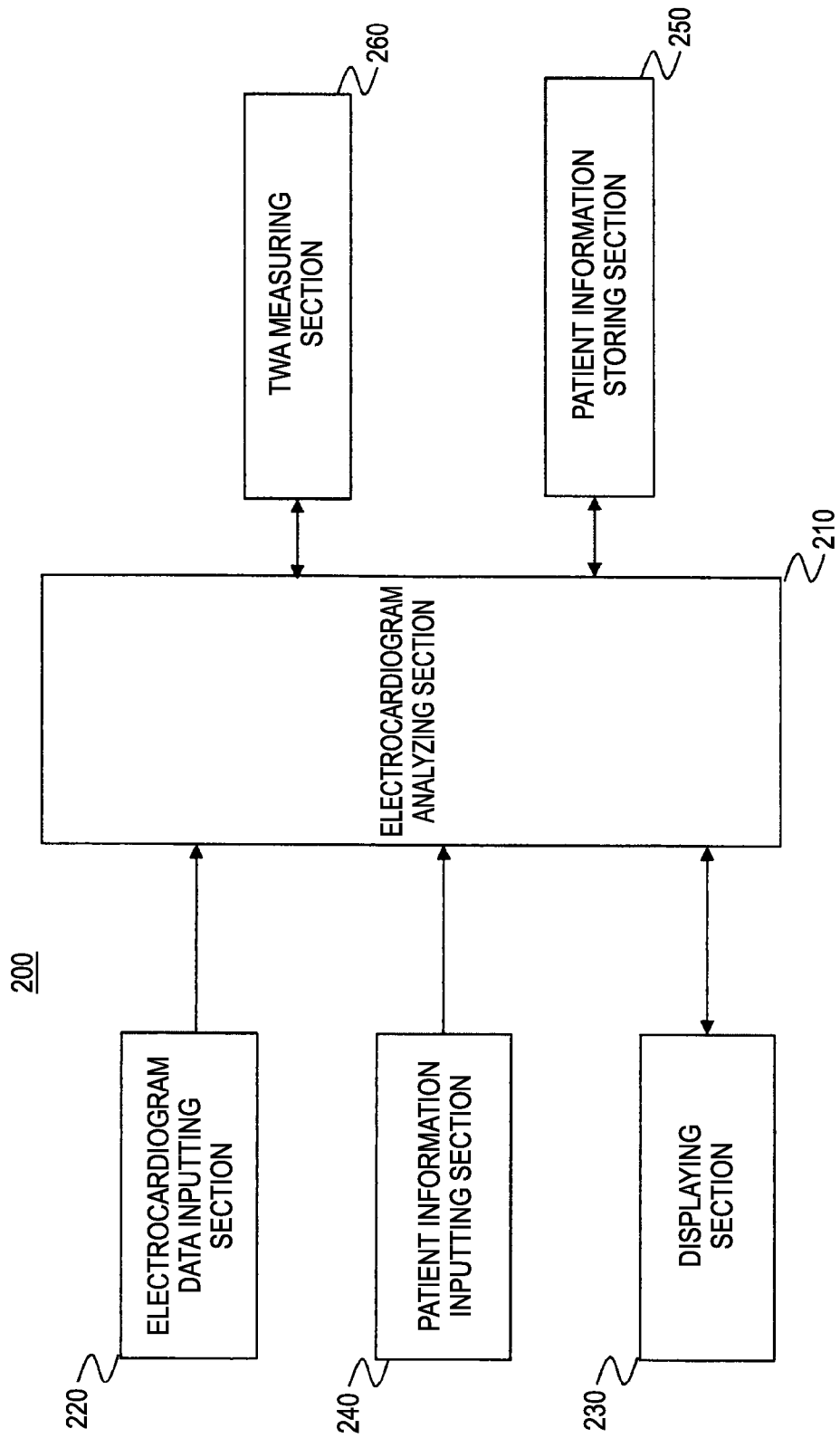
FIG. 12 is a block diagram of TWA measuring apparatuses of Embodiments 3 and 4.

FIG. 12 is a block diagram of the TWA measuring apparatus of Embodiment 3.

As shown in the figure, the TWA measuring apparatus 200 includes an electrocardiogram analyzing section 210, the electrocardiogram data inputting section 220, a displaying section 230, a patient information inputting section 240, a patient information storing section 250, and a TWA measuring section 260.

The electrocardiogram analyzing section 210 generally controls the operations of the electrocardiogram data inputting section 220, the displaying section 230, the patient information inputting section 240, the patient information storing section 250, and the TWA measuring section 260. The specific configuration of the electrocardiogram analyzing section 210 is identical with the block diagram of FIG. 2.

The electrocardiogram data inputting section 220 inputs electrocardiogram data which are collected by a Holter electrocardiograph or a monitoring electrocardiograph. The input electrocardiogram data are stored in the electrocardiogram analyzing section 210.

The displaying section 230 displays patient information which is supplied from the patient information inputting section 240, and which is stored in the patient information storing section 250, and a measurement result of the presence of TWA.

The patient information inputting section 240 is used for inputting patient information by means of key operations of the measuring person. The patient information contains a patient ID, the name of the patient, the age of the patient, and the sex of the patient.

The patient information storing section 250 stores the patient information which is input through the patient information inputting section 240, namely, the patient ID, the name of the patient, the age of the patient, and the sex of the patient.

The TWA measuring section 260 measures in detail variations of the heartbeat by using the electrocardiogram data stored in the electrocardiogram analyzing section 210, to measure the presence of TWA.

(Operation of TWA Measuring Apparatus)

Figure 13:
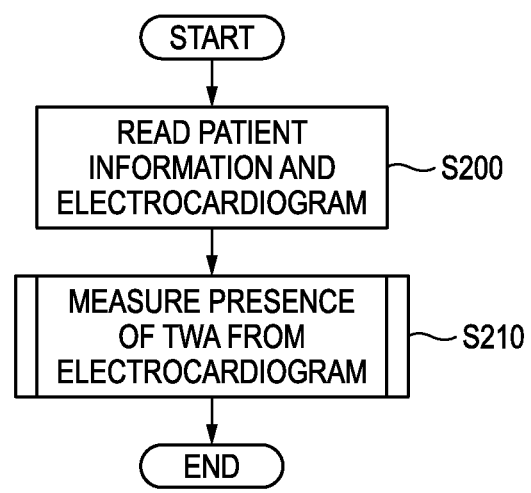
FIG. 13 is an operation flowchart of the TWA measuring apparatuses of Embodiments 3 and 4.

Next, the operation of the TWA measuring apparatus of Embodiment 3 will be described. FIG. 13 is an operation flowchart of the TWA measuring apparatuses of Embodiment 3.

<Step S200>

The operator of the TWA measuring apparatus 200 (computer) shown in FIG. 12 connects a Holter electrocardiograph or a monitoring electrocardiograph to the electrocardiogram data inputting section 220, and the electrocardiogram analyzing section 210 reads electrocardiogram data from the connected electrocardiograph. The electrocardiogram analyzing section 210 further reads patient information which is input by the operator through the patient information inputting section 240. The read electrocardiogram data are stored in the electrocardiogram analyzing section 210, and the input patient information is stored in the patient information storing section 250.

<Step S210>

The TWA measuring section 260 measures the presence of TWA from electrocardiogram waveforms contained in the read electrocardiogram waveforms. The specific process of the step is identical with the processes of the flowcharts of FIGS. 4 to 6.

In Embodiment 3, similarly with Embodiment 1, the presence of TWA can be accurately measured from electrocardiogram data which are collected for a long time period by a Holter electrocardiograph or a monitoring electrocardiograph.

Embodiment 4

Hereinafter, a TWA measuring apparatus and TWA measuring method of Embodiment 4 will be described. In the embodiment, an electrocardiogram data inputting section is disposed in place of the measurement electrodes 120 in Embodiment 2. The processes performed until when, based on the acquired electrocardiogram waveforms, it is determined whether the presence of TWA exists or not are identical with those of Embodiment 2. Namely, the processes which are identical with the processes shown in the flowcharts of FIGS. 3 to 6 are performed.

Although the TWA measuring apparatus of Embodiment 2 is disposed in the electrocardiograph, that of the embodiment is disposed in a computer instead of the electrocardiograph. The embodiment is employed in the case where, as in an electrocardiogram such as a Holter electrocardiogram or a monitoring electrocardiogram, data are collected for a long time period, and downloaded into the computer to be used in determining whether TWA exists or not.

The configuration of the TWA measuring apparatus of the embodiment is identical with the block diagram of FIG. 12. Moreover, the operation of the TWA measuring apparatus of the embodiment is generally identical with the flowchart of FIG. 13.

In Embodiment 4, similarly with Embodiment 2, the presence of TWA can be accurately measured from electrocardiogram data which are collected for a long time period by a Holter electrocardiograph or a monitoring electrocardiograph.

According to an aspect of the presently disclosed subject matter, the heartbeat condition is determined by statistically processing the electrocardiogram waveforms which are acquired in increments of a constant beat number, and, if it is determined that the heartbeat condition is unstable, the variation in heartbeat is measured in detail. Therefore, TWA can be accurately measured.

What is claimed is:

1. A T-wave alternans (TWA) measuring apparatus comprising:
   a non-transitory computer readable storage medium configured to store a plurality of software instructions; and
   a processor programmed to execute said plurality of software instructions, said plurality of software instructions comprising:
      a grouping section which is configured to group electrocardiogram waveforms of a subject in increments of a first beat number, to generate a plurality of first groups;
      a storage section which is configured to store the electrocardiogram waveforms;
      a testing section which is configured to test a statistical intergroup difference of measurement values of the electrocardiogram waveforms of the first groups;
      a heartbeat condition determining section which is configured to determine that a heartbeat condition is unstable, when a significant statistical difference exists between the first groups; and
      a TWA measuring section which is configured to measure, when it is determined that the heartbeat condition is unstable, variation in heartbeat by using the electrocardiogram waveforms which are stored in the storage section,
   wherein
      the electrocardiogram waveforms are acquired from the subject,
      the grouping section groups the electrocardiogram waveforms in increments of a second beat number, which is different from the first beat number, to generate a plurality of second groups,
      the testing section tests a statistical intergroup difference of measurement values of the electrocardiogram waveforms of the second groups,
      the heartbeat condition determining section determines that the heartbeat condition is unstable, when a significant statistical difference exists between the first groups and a significant statistical difference does not exist between the second groups, and
      the electrocardiogram waveforms of the first groups and second groups are the electrocardiogram waveforms which are stored in the storage section.

2. The TWA measuring apparatus according to claim 1, wherein
   the first beat number is a constant beat number.

3. The TWA measuring apparatus according to claim 2, wherein the first beat number is a prime beat number.

4. The TWA measuring apparatus according to claim 1, further comprising:
   an electrocardiogram data inputting section which is configured to input electrocardiogram data including the electrocardiogram waveforms of the subject,
   wherein the first beat number is a constant beat number.

5. The TWA measuring apparatus according to claim 4, wherein the first beat number is a prime beat number.

6. The TWA measuring apparatus according to claim 1, further comprising:
   an electrocardiogram data inputting section which is configured to input electrocardiogram data including the electrocardiogram waveforms of the subject.

7. The TWA measuring apparatus according to claim 6, wherein each of the first beat number and the second beat number is a prime beat number.

8. The TWA measuring apparatus according to claim 1, wherein the electrocardiogram waveforms grouped by the grouping section are electrocardiogram waveforms of a constant beat number.

9. The TWA measuring apparatus according to claim 1, wherein each of the first beat number and the second beat number is a prime beat number.

10. The TWA measuring apparatus according to claim 1, wherein the TWA measuring section performs FFT processing on a constant number of electrocardiogram waveforms in the electrocardiogram waveforms stored in the storage section to calculate a periodogram, calculates an alternans value by using the calculated periodogram, and determines presence of TWA by using the alternans value.

11. The TWA measuring apparatus according to claim 1, wherein the TWA measuring section extracts a constant number of electrocardiogram waveforms in the electrocardiogram waveforms stored in the storage section, produces typical waveforms of odd and even beats of the extracted electrocardiogram waveforms, and compares the typical waveforms of odd and even beats with each other, thereby determining presence of TWA.

12. The TWA measuring apparatus according to claim 1, wherein
   the first beat number is 2, and
   the second beat number is a prime beat number other than 1.

13. A T-wave alternans (TWA) measuring method comprising:
   grouping electrocardiogram waveforms of a subject in increments of a first beat number, to generate a plurality of first groups;
   storing in a storage section the electrocardiogram waveforms;

testing a statistical intergroup difference of measurement values of the electrocardiogram waveforms of the first groups;

determining that a heartbeat condition is unstable, when a significant statistical difference exists between the first groups;

measuring variation in heartbeat, when it is determined that the heartbeat condition is unstable, by using the electrocardiogram waveforms which are stored in the storage section;

attaching measurement electrodes to acquire the electrocardiogram waveforms from the subject;

grouping the electrocardiogram waveforms in increments of a second beat number, which is different from the first beat number, to generate a plurality of second groups; and testing a statistical intergroup difference of measurement values of the electrocardiogram waveforms of the second groups, wherein it is determined that the heartbeat condition is unstable, when a significant statistical difference exists between the first groups and a significant statistical difference does not exist between the second groups, and wherein the electrocardiogram waveforms of the first groups and second groups are the electrocardiogram waveforms which are stored in the storage section.

14. The TWA measuring method according to claim 13, wherein the first beat number is a constant beat number.

15. The TWA measuring method according to claim 13, further comprising:
inputting electrocardiogram data including the electrocardiogram waveforms of the subject,
wherein the first beat number is a constant beat number.

16. The TWA measuring method according to claim 13, further comprising:
inputting electrocardiogram data including the electrocardiogram waveforms of the subject.

17. The TWA measuring method according to claim 13, wherein
a process of measuring the variation in heartbeat includes:
performing FFT processing on a constant number of electrocardiogram waveforms in the electrocardiogram waveforms to calculate a periodogram;
calculating an alternans value by using the calculated periodogram; and
determining presence of TWA by using the alternans value.

18. The TWA measuring method according to claim 13, wherein
a process of measuring the variation in heartbeat includes:
producing typical waveforms of odd and even beats by using a constant number of electrocardiogram waveforms in the electrocardiogram waveforms; and
comparing the typical waveforms of odd and even beats with each other, thereby determining presence of TWA.

* * * * *